United States Patent [19]

Krueger et al.

[11] 4,044,793
[45] Aug. 30, 1977

[54] RELIEF VALVE

[75] Inventors: Kenneth Keith Krueger, Tustin; Todor Pavlov, Laguna Niguel, both of Calif.

[73] Assignee: Shiley Laboratories, Inc., Irvine, Calif.

[21] Appl. No.: 607,265

[22] Filed: Aug. 25, 1975

[51] Int. Cl.² .............................................. F16K 11/20
[52] U.S. Cl. .................................. 137/612.1; 128/351; 128/349 BV; 137/508; 141/46; 141/302
[58] Field of Search ............ 128/349 BV, 350 V, 351, 128/349 R; 137/508, 494, 493.1, 493.2, 493.3, 493.9, 226, 612.1; 141/46, 302, 348, 349

[56] References Cited

U.S. PATENT DOCUMENTS

| | | | |
|---|---|---|---|
| 1,608,618 | 11/1926 | Richards | 137/508 |
| 3,229,716 | 1/1966 | Johnson et al. | 137/612.1 |
| 3,406,682 | 10/1968 | Engstrom | 128/145.8 |
| 3,478,743 | 11/1969 | Ericson | 128/349 BV |
| 3,491,786 | 1/1970 | Crossman et al. | 137/226 |
| 3,794,043 | 2/1974 | McGinnis | 128/351 |
| 3,841,348 | 10/1974 | O'Neill | 137/494 |
| 3,910,270 | 10/1975 | Stewart | 128/145.8 |

Primary Examiner—Robert W. Michell
Assistant Examiner—Henry J. Recla
Attorney, Agent, or Firm—Knobbe, Martens, Olson, Hubbard & Bear

[57] ABSTRACT

A relief valve having a main passage normally closed with a main valve member and a vent passage normally closed with a vent valve member, the vent valve member being constructed to open the vent passage upon application of a predetermined pressure into the main valve passage to thereby prevent application of greater than said predetermined pressure to the outlet of the valve is disclosed.

24 Claims, 3 Drawing Figures

RELIEF VALVE

Related Patent Applications

U.S. Application Ser. No. 607,231, filed concurrently herewith entitled TRACHEOSTOMY TUBE WITH PRESSURE RELIEF VALVE and U.S. Pat. application Ser. No. De. 607,264, filed concurrently herewith entitled VALVE DESIGN.

This invention relates to relief valves, and, more specifically to valves adapted to prevent the application of greater than a predetermined pressure to the outlet of the valve.

Pressure reducing valves in which a biased diaphragm actuated valve automatically meters the rate of flow of fluids through an orifice to thereby limit the applied pressure are well know. Diaphragm actuating elements for valves are found in many types of valves and fluid control systems for limiting or metering the amount of flow, for controlling pressure, and for many other purposes. The present invention comprises an improvement in diaphragm actuated pressure relief valves.

It is important in some fluid systems to prevent more than a predetermined pressure from being applied to a particular system or element. For example, as more fully described in my aforesaid copending application entitled TRACHEOSTOMY TUBE WITH PRESSURE RELIEF VALVE, it is important to prevent more than a predetermined pressure from being applied to an in-dwelling retaining balloon of a tracheostomy tube, or the like. Similarly, retention catheters having an expansible element may require that no more than a maximum pressure be applied thereto. In these systems, the amount of fluid involved is comparatively small and, therefore, it is important that pressure regulating means be sensitive to small changes in pressure. In other systems, for example in anesthesia control systems, breathing systems, and the like, greater volumes of fluid are involved but pressure control may be equally important.

In addition, in some systems, such as the one described in my aforesaid copending patent application, the entire system is made in a disposable form, since sterilization and re-use is often impractical or impossible. Consequently, it is all of the greatest importance that any regulatory valve system which may be included therein be simply and inexpensively constructed. The valve described herein was designed particularly for application in disposable systems of the type referred to; however, its utility and value is not limited thereto.

One of the important features of the present invention is that the valve is small in size and yet extremely sensitive to pressure changes. Consequently, the valve is very effective in limiting the maximum pressure which may be applied at the outlet of the valve.

Another important feature of the present invention is that the valve described and claimed herein can be manufactured on a very large scale production basis at a very low cost with high repeatability as to pressure sensitivity and high reliability.

Another feature of the invention is that the valve described and claimed herein can be manufactured in a comparatively small configuration, no more than an inch or an inch and a half in diameter, for example, and yet perform reliably and repeatably.

In brief summary, the relief valve of this invention comprises a valve body which has a fluid inlet and a fluid outlet connected to each other through means forming a main passage through the valve. The main passage is normally closed by a main valve which is disposed and located in the main fluid passage. A vent passage system is provided in the valve in fluid communication with the main passage and with the exterior of the valve body, or to some other venting system. The vent system includes a vent valve normally closing the vent passage. The vent valve comprises a flexible valving member so constructed and disposed as automatically to open the vent passage when the pressure in the main passage applied through the vent passage and on the flexible valve member reaches a predetermined value. Once the vent passage is opened, fluid escapes from the main passage through the vent passage and past the vent valve thereby reducing the pressure applied through the main passage of the valve and preventing fluid pressure of greater than the predetermined value from being applied at the outlet of the main fluid passage.

There are many important and many convenient structural and functional features and relationships which will be apparent from the specification and the drawings.

In the Drawings

Figure 1:
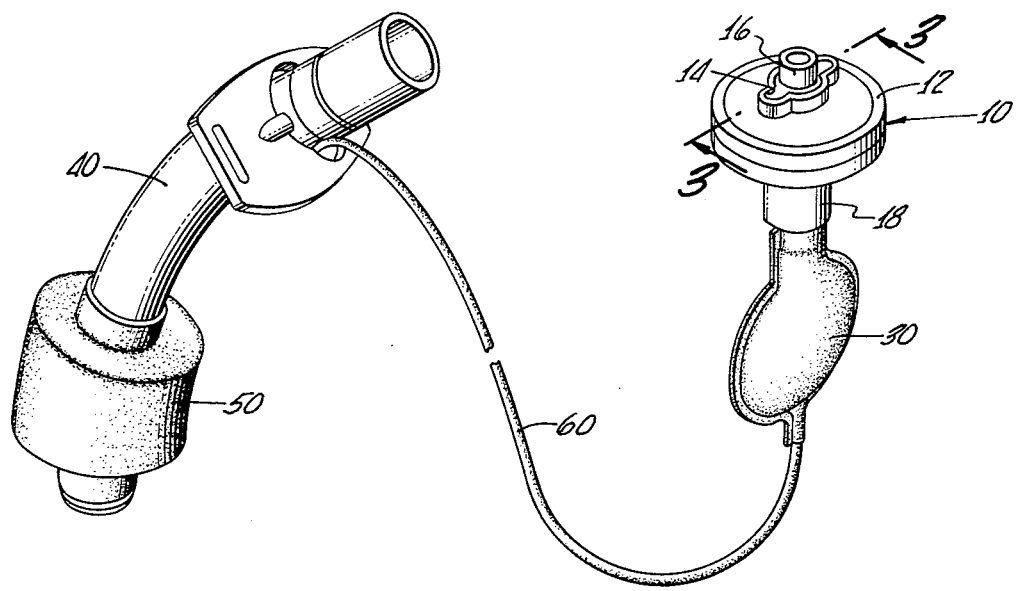
FIG. 1 illustrates a tracheostomy tube assembly of this invention finds particular utility.
Figure 3:
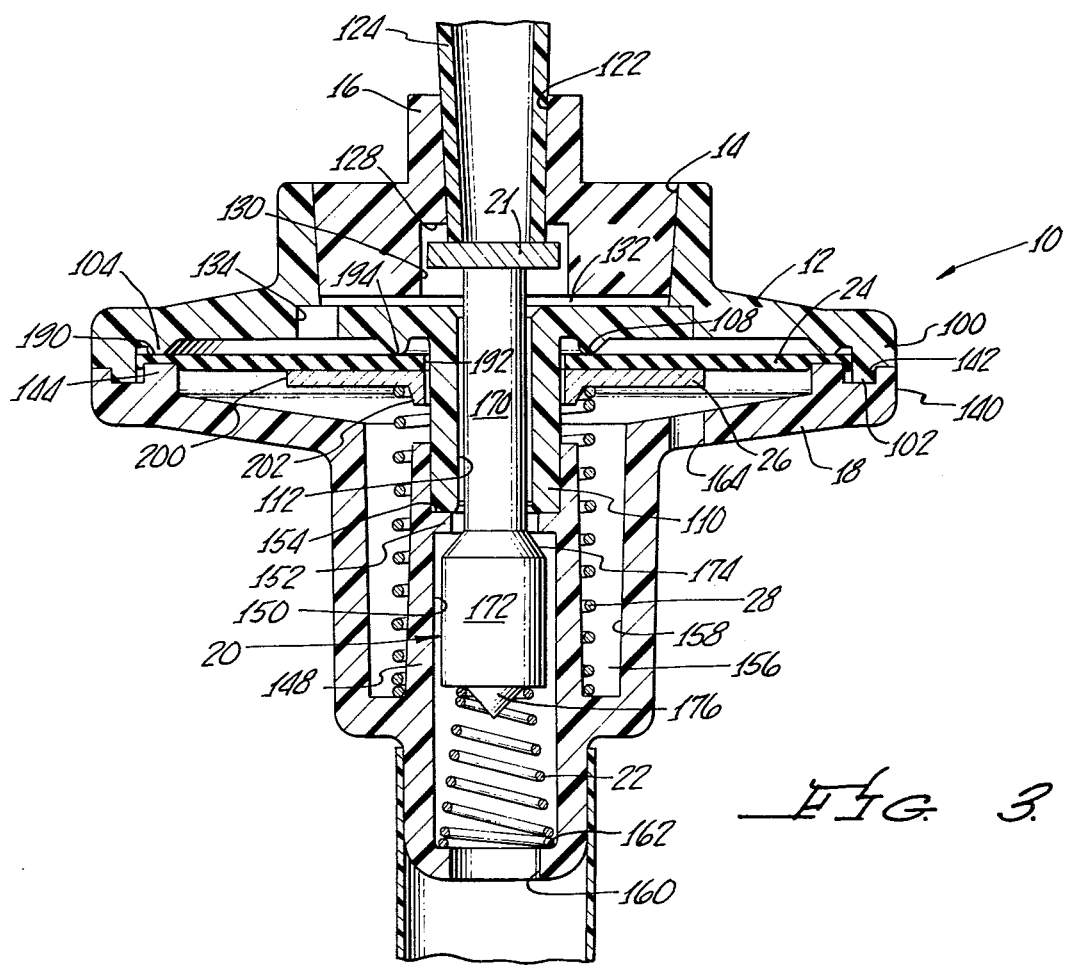
FIG. 3 depicts the valve in cross-section having a luer tip inserted therein and the main valve in open position.
Figure 2:
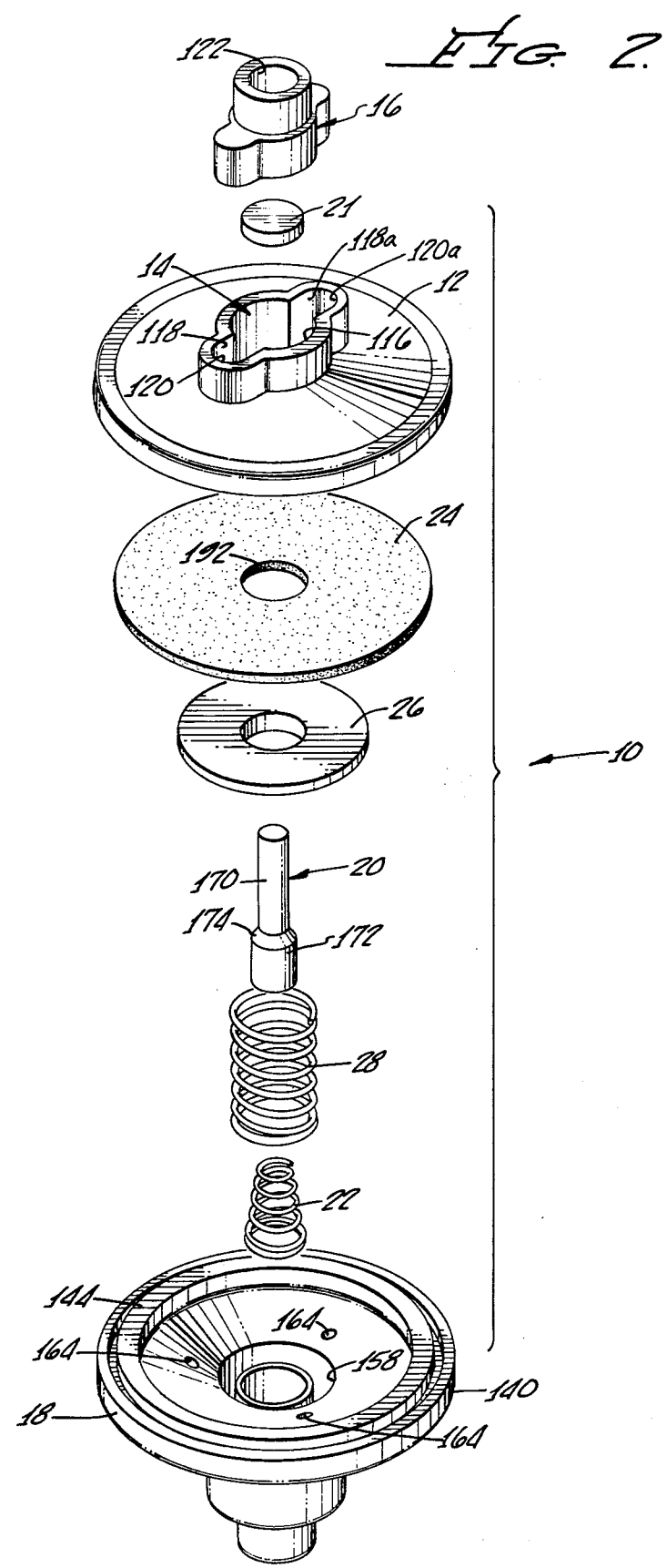
FIG. 2 depicts the improved valve which is an important aspect of this invention with its components in exploded isometric view.

The major components of the tracheostomy system which is the exemplary and illustrative embodiment of the overall invention described herein include the pressure relief valve 10, which will be described in complete detail hereinafter, the indicator balloon 30, the tracheostomy cannula 40, including the retention cuff 50 connected by a fluid conduit 60 to the indicator balloon and the pressure relief valve. Pressure is conventionally applied by means of a syringe, however, any other pressure applying means may be used.

It will be understood that the illustrative embodiment exemplifies only one preferred form of the invention and that, in lieu of the tracheostomy tube, balloon or cuff equipped cannula generally such as embolectomy catheters, indwelling catheters, ureteral catheters and the like, and other devices which are equipped with inflatable cuffs, balloons or other elements which are inflated in the body or in other locations where they are not visible may be used in connection with the present invention.

The tracheostomy tube including the cuff and the indicator balloon may, in the exemplary form of the invention, be of the type described in the aforesaid patent of Donald P. Shiley.

With reference to the figures generally, the valve 10 comprises an inlet member 12 having an opening 14 adapted to receive luer adapter inlet 16, and an outlet member 18. The valve also includes a main valving member 20 received in a main passage of the valve, a flow restriction and air filter 21 between the main valve member 20 and the inlet, a spring 22 biasing the main valve to the normally closed position, and a vent valve assembly which includes a diaphragm 24, a washer 26 and a spring 28 which biases the washer and the diaphragm to the normally closed position.

It will be apparent from the general description that there are many ways of constructing and assemblying the valve. It will also be apparent that various equivalent structures, elements, and means may be used to accomplish the same functions in substantially the same way. For example, while a compression spring is illustrated as the biasing means for both of the main valves and the vent valve, their biasing means generally would be equivalent. In addition, while a flat, annular diaphragm is illustrated, other flexible means would perform and function in an equivalent manner in the same or equivalent structural and functional combination. The best mode of making and using the invention presently known to the inventors is described as the preferred embodiment; however, the invention is not limited to the preferred embodiment, which is described in considerable detail to exemplify and illustrate the best mode for carrying out the invention and not in any respect for limiting the invention thereto.

In the exemplary, illustrative embodiment shown in the drawings, the inlet member is generally circular in configuration since this provides aesthetically advantageous features as well as functional efficiency. Adjacent the periphery 100 and spaced slightly inwardly is an annular ridge 102 which is adapted to be received in a groove in the outlet member, which will be described in detail hereinafter, during assembly of the valve. On the inside of the inlet member, adjacent the rib 102 and spaced slightly inwardly therefrom is a raised peripheral ridge 104 which cooperates with a ridge on the outlet member, which will be described hereinafter in detail, for sealing therebetween the diaphragm 24. The surface 106 is annular in configuration and defines the space between the diaphragm sealing ridge 104 and a valve seat ridge 108 which is interior to and, in the preferred embodiment, concentric with the diaphragm sealing ridge 104.

Also concentric with the diaphragm sealing ridge 104, in the preferred embodiment, and interior of the ridge 108 is a tubular main fluid conductor extension 110 which forms therethrough the main fluid passage 112, in which is loosely received the valve member 20.

On the other side of the inlet member 12 there is formed the opening 14 for receiving the luer tip adapter 16. In the preferred embodiment, the luer tip opening is generally circular in configuration as indicated at 116 with side openings 118 and 118a having rounded ends 120 and 120a and the luer tip adapter is of similar size and configuration for being received and adhesively secured therein. Of course, the luer tip adapter and the inlet member may be fashioned of more than two pieces or of less than two pieces, depending upon the manufacturing technique desired. The luer tip adapter has a luer inlet 122 whick is adapted to receive a luer, indicated at 124, tightly therein to permit fluid communication from the interior of the syringe to the main passage, as will be described hereinafter. The inlet 122 widens at a shoulder 128 to a larger inlet passage 130. The restriction 21 is adapted to be received in the enlarged inlet passage 130 adjacent the seat 128 formed by the juncture of inlet passage portions 122 and 130. The flow restriction 21 may be simply a flat circular or other configuration porous disc or a porous plug of any other desired configuration depending upon the desired shape, size and configuration of the inlet passage and the valve element 20. The function of the restriction 21 will be described in more detail hereinafter.

In the preferred embodiment, the luer tip adapter 16 is so constructed and disposed in the opening as to provide a space forming a passage 132 extending outwardly from the passage 130 and in fluid communication with an opening 134 through the inlet member into an inlet portion of a chamber defined by the wall 106, the diaphragm 24, and the ridges 104 and 108, all of which are in the vent passage system as will be described hereinafter.

The outlet member 18 is, in the preferred embodiment, likewise circular in configuration for aesthetic purposes which are consistent with the efficiency of material use and functional characteristics. Slightly inwardly of the periphery 140 is a groove 142 which receives the ridge 102 of the inlet member. In the preferred method of assembly, the ridge 102 and the groove 142 are ultrasonically welded together, after the diaphragm, washer, etc. are properly positioned in place. Still further inwardly of the periphery 140 and the groove 142 is a ridge 144 which is annular in configuration and constructed and adapted to cooperate with the diaphragm sealing ridge 104 on the inlet number to secure and seal therebetween the edge of the diaphragm 24. The diaphragm 24 may be held in position by the compressive force applied between the diaphragm sealing edges 104 and 144 or by adhesive applied between the ridges 104 and 144 and the diaphragm 24, or by a combination of compressive and adhesive securement, or by other means. An annular tubular portion 148 forms a main passage portion 150 which, in the preferred embodiment, is generally co-axial with the main passage portion in the inlet member. The outlet member also forms a valve seat 152. In the preferred embodiment, the annular tubular portion forming the main passage portion in the outlet member is constructed and adapted to mate with the conductor extension forming the main passage portion of the inlet member so as to connect to two main passage portions into a single main passage separate from the chamber which surrounds the main passage. In the preferred embodiment, this mating is in the form of a shoulder joint 154 between the distal end of the annular tubular portion of the outlet member and the conductor extension of the inlet member. A fluid tight mating seal may be formed by precision contact, a compression sealing member such as an O-ring or washer, or by adhesively securing the two elements together, as may be preferred in any particular assembly method.

An annular chamber portion 156 is formed between the annular tubular portion 148 and the wall 158 of the outlet member, the function of which will be described in detail hereinafter.

The outlet includes an outlet opening 160, the juncture between the passage 150 and the outlet opening 160 forming an annular shoulder 162, the function of which will also be described later. One or more vent openings 164 are provided to permit fluid communication from exterior of the valve body, or to some other venting means, and the vent chamber defined by the wall of the outlet member, the diaphragm 24, rib 144, and by combination of the conductor extension 110, the tubular portion 148 and the wall 158. This outlet chamber forms a part of the vent system as will be described hereinafter.

The valve element 20 is generally cylindrical in nature having an elongate cylindrical portion 170 extending loosely through and in spaced relationship with respect to the walls of the main passage portion 112 and into the inlet passage portion 130. The valve also includes an enlarged cylindrical portion 172 joined with the cylindrical portion 170 by a beveled or tapered face 174, the latter forming a valve surface for contact with the valve seat 152. In the preferred embodiment, a short boss 176 extends on the other side of the shoulder 172 for receiving and positioning the compression spring 22 which is held in compression between the valve 20 and the shoulder 162 to provide resilient biasing of the valve 20 into the closed position, with the seat 152 and the valving surface 174 in contact. In the preferred embodiment, the extension 170 is generally cylindrical in configuration although a slightly frusto-conical configuration may be slightly advantageous in providing freedom of movement.

In the preferred embodiment, the diaphragm 24 is simply an annular flexible member having an outer circumferential portion 190 secured between the ribs 104 and 144 as previously described and an inner annular circumferential portion 192 received around the conductor extension of the inlet member and spaced therefrom slightly to permit fluid flow between the diaphragm and the conductor extension as part of the vent passage system. It is desirable to provide an annular washer 26 which has a generally flat outer annular portion 200 extending from an inner annular sleeve 202 which surrounds the conductor extension in spaced relationship substantially in the manner described with respect to the inner circumferential portion 192 of the diaphragm. The washer 26 maintains the diaphragm in substantially flat configuration and provides a uniform surface for exerting a resilient closing force from the spring 28, which is received around the sleeve portion 202, against the annular portion 200 at one end and in the annular chamber portion 156 at the other end. The resilient force provided by the compression coil spring 28 is exerted through the washer 26 to the diaphragm 24 to an internal annular portion 194 adjacent the internal circumference 192. The contact between the annular valve portion 194 of the diaphragm 24 and the rib 108 of the inlet member 12 provides the vent valve action.

Operation

In operation, the valve outlet member is connected to a tracheostomy cuff, which requires that applied pressure not exceed a predetermined value.

Fluid pressure applying means, such as a nozzle connected through a fluid conduit to a source of pressurized or convenient fluid source, is inserted in the inlet. In describing the operation of the valve hereinafter, reference will be made to the use of a syringe with a luer tip for opening the main passage valve, but it will be understood that any other fluid pressure applying means can be used in an equivalent manner.

As the luer tip is inserted into the inlet, the tip contacts the restriction 21 through which the fluid is filtered. If filtering is not required, the valve can be actuated directly. In either event, the valve 20 would be moved away from the inlet, separating the valve face portion 174 from the valve seat 152, thereby opening the main valve and permitting fluid flow through the main passage of the valve from the inlet, through the main passage past the main valve to the outlet of the valve and into the cuff. Thus, the main passage system permits the application of pressurized fluid to a cuff upon insertion of the leur or other pressure applying means into the inlet.

In order to limit the pressure which is applied to the outlet of the valve and to the cuff to a predetermined value, a vent passage system including the passage 132 which is in communication with the main passage through an opening 134 into an inlet portion, defined by wall 106, diaphragm 24 and ribs 104 and 108 of a chamber surrounding the main passage. When the pressure applied against diaphragm 24 reaches the predetermined value, the diaphragm 24 is moved by the pressure on the diaphragm such that the annular valving portion 194 of the diaphragm is spaced from the valve seat ridge 108 to permit fluid flow through the valve, through the annular passage formed by the space between the diaphragm inner circumference 192 and the conductor extension 110, into the outlet portion of the chamber surrounding the main passage defined by the other side of diaphragm 24, ridge 144, the conductor extension 110 and tubular portion 148, wall 158 and the wall portion 166 of the outlet member and through vent 164 outside of the valve body. Fluid will flow so long as the pressure in the main passage is above the predetermined value for opening the vent valve. The effect of opening the vent valve is to maintain the pressure in the main passage to substantially the predetermined value required to open the vent valve. The amount of gas flowing through the vent system will depend upon the level of pressure applied to the inlet of the valve, but the pressure applied at the outlet of the valve will remain at substantially the predetermined pressure required to open the vent valve within a broad range of pressures applied to the inlet.

It will be understood that the venting action of the valve may not be to the exterior of the actual body but simply into another venting or passage system which, of course, would be equivalent to venting outside the body as described herein.

The pressure required to open the vent valve may be predetermined by selecting compression spring 28 requiring the predetermined force to compress the spring. In addition, the diaphragm 24 may be made of a semi-rigid material, such as phosphor bronze, brass, or other spring-type material in which additional biasing means in the form of compression spring 28 would not be required, the normally closed position being attained by the natural configuration of the diaphragm. Other means for maintaining the vent valve in normally closed position, such as extension springs, resilient bodies, etc., connected to or bearing against the diaphragm may be provided as desired.

In the preferred embodiment the valve body is preferably injection molded of polypropylene, delrin, ABS resin, or other desired material and the diaphragm is preferably of neoprene, or other soft, resilient material. The springs may be fabricated of virtually any material, but are preferably of a non-corrosive material which is compatible, at least for short times, with body fluids, although this is not a requirement in many applications. Stainless steel springs or springs formed of various plastics, such as nylon, delrin, etc., may be used where biological inertness is desired.

One of the important features of the valve is that it prevents any reverse flow from the cuff through outlet of the valve through the main passage except when a pressure applying device, such as a syringe, is connected to the inlet. Another important feature is that the vent is connected only to the main passage between the main valve and the inlet so that the vent system and pressure controlling means therein becomes operational only when the fluid source, e.g. the luer tip, is in the inlet of the valve.

In the preferred embodiment, as illustrated, the vent valve and pressure regulating system includes a diaphragm in which the valving surface is near the center of the diaphragm, proximate the interior circumference of the annular diaphragm in the preferred embodiment. Of course, the diaphragm may be secured adjacent the interior circumference or other portions of the diaphragm with the valving action taking place near the exterior of the diaphragm or at other portions thereof.

The example given above in which the valve is used as part of an improved tracheostomy tube system is, of course, merely illustrative of a typical use. The valve finds utility and application in many other systems, including medical apparatus such as usage in connection with retention balloons of all types.

It will be apparent from the foregoing discussion and from the illustrations that there are many variations which can be made of the various elements, combinational and constructional features of the illustrative embodiment without departing from the spirit and scope of the invention as defined in the following claims.

We claim:

1. A relief valve for preventing greater than a predetermined fluid pressure from being applied through a main passage to the outlet of the valve, comprising, in combination:
    a generally circular inlet member having on one side, peripheral diaphragm sealing ridge, an annular valve seat ridge interior to and concentric with the diaphragm sealing ridge, and a tubular main fluid conductor extension having a main fluid passage therein, said conductor being interior to and concentric with the valve seat ridge, said inlet member also forming, on the other side, an opening for receiving a luer tip adapter and a passage through the inlet member in communication with the luer tip receiving opening and the annular space between the diaphragm sealing ridge and the valve seat;
    a luer tip adapter received in the opening therefore in the inlet member, said luer tip adapter having a luer inlet therethrough in fluid communication with the main fluid passage and with the passage to the space between the diaphragm and the valve seat;
    a generally circular outlet member having a diaphragm sealing ridge constructed and adapted to cooperate with the diaphragm sealing ridge on the inlet member to secure and seal between said ridges the edge of a diaphragm, an annular tubular portion defining a main passage generally coaxial with the main passage in the inlet member, said main passage being in communication with an outlet on the opposite side of an in generally coaxially with the luer tip inlet, a valve seat formed in the main passage, the annular tubular portion being constructed and adapted to mate with the conductor extension of the inlet member for thereby forming the main fluid passage through the valve from the luer tip inlet through the main fluid passage to the outlet, the outlet member including at least one vent opening spaced laterally from the tubular portion;
    a movable generally cylindrical main valve member disposed for axial movement in the main fluid passage, the main valve member having thereon a shoulder valving portion which seats, in the closed position, against the seat and having one end which extends through the main passage in the inlet member in spaced relation to the walls of the main passage to a point proximate the inside of the luer inlet for being moved axially upon insertion of a luer tip into the luer inlet to thereby move the shoulder away from the seat to open the main valve;
    a coil compression spring bearing resiliently against the main valve member for resiliently biasing the main valve to the normally closed position;
    an annular diaphragm sealed at its edges between the diaphragm sealing ridges of the inlet and the outlet members having an opening in the center thereof through which the conductor extension of the inlet member extends in spaced relation to the inside edge of the annular diaphragm, the portion adjacent the central opening forming a valving member for contacting the seat ridges on the inlet member;
    an annular washer surrounding the conductor disposed on the opposite side of the diaphragm from the portion which contacts the seat ridges;
    a compression spring bearing against the washer and received around the tubular portion of the outlet member for resiliently biasing the washer and the valving portion of the diaphragm toward the valve seat ridges; and
    the passage through the luer inlet, through the inlet member, between the inside edge of the diaphragm and the conductor extension, and through the vent opening, forming a vent passage which is normally closed by the vent valve comprising the diaphragm valving portion and the seat ridge on the inlet member, the resiliency of the spring and of the diaphragm requiring a predetermined pressure to open the vent valve, the main passage being defined by the luer inlet, the luer tip receiving opening, the passage through the conductor extension of the inlet member and the tubular portion and outlet of the outlet member, whereby upon insertion of a luer into the luer inlet the main valve is opened and upon application of fluid pressure into the luer inlet above predetermined pressure value the vent opens the vent passage to thereby prevent application of pressure above said predetermined pressure valve from being applied through the main passage to the outlet.

2. A relief valve for use with pressure applying means for preventing greater than a predetermined fluid pressure from being applied through a main passage to the outlet of the valve, comprising, in combination:
    a valve body having an inlet and an outlet in fluid communication with each other through means forming a main passage extending through the valve body;
    main valve seat means formed in the main passage;
    main valving means movably received in the main passage including means actuatable by said pressure applying means for moving said main valving means from a normally closed position in contact with the valve seat to an open position;
    a chamber surrounding the main passage;
    vent valving means dividing the chamber into a first side and a second side;
    the valve body having a bypass passage between the main passage and the first side of the chamber upstream of said main valve seat means and a vent passage from the second side of the chamber to the exterior of the body; and vent valve seat means formed between said first and second sides for being engaged by the vent valving means in the closed position;

the vent valving means being so constructed and disposed to move from the vent valve seat means only upon application of a predetermined fluid pressure through the bypass passage from the main passage for permitting fluid to escape from the main passage through the vent system formed by the bypass and vent passages and the vent valve, whereby no greater than said predetermined pressure is applied through the main pressure to the outlet of the valve.

3. A relief valve for use with pressure applying means for preventing greater than a predetermined pressure from being applied through a main passage to the outlet of the valve, comprising, in combination:

a valve body having an inlet and an outlet in fluid communication with each other through means forming a main passage extending through the valve body;

main valve seat means formed in the main passage between said inlet and outlet; main valving means movably received in the main passage including means actuatable by said pressure applying means for moving said main valving means from a normally closed position in contact with the valve seat to an open position, said main valving means including means extending proximate the inlet to the main passage for being moved by fluid pressure applying means inserted into said inlet for thereby opening the main valve;

a chamber surrounding the main passage;

vent valving means dividing the chamber into a first side and a second side;

the valve body having a bypass passage between the main passage and the first side of the chamber upstream of said main valve seat means and a vent passage from the second side of the chamber to the exterior of the body;

vent valve seat means formed between said first and second sides for being engaged by the vent valving means in the closed position; and the vent valving means being so constructed and disposed to move from the vent valve seat means only upon application of a predetermined fluid pressure through the bypass passage from the main passage for permitting fluid to escape from the main passage through the vent system formed by the bypass and vent passages and the vent valve, whereby no greater than said predetermined pressure is applied through the main passage to the outlet of the valve.

4. The valve defined in claim 3 wherein the bypass passage communicates with the main passage between the main valve and the inlet whereby the vent system is in fluid communication with the outlet only when the main valve is open.

5. The valve defined in claim 4 wherein the vent valving means comprises a flexible member constructed and adapted to move from a closed position in contact with the vent valve seat means to an open position spaced therefrom.

6. The valve defined in claim 5 wherein the vent valving means is an annular diaphragm surrounding the means forming the main passage.

7. The valve defined in claim 6 wherein the vent valve seat is an annular ridge formed in the body around the means forming the main passage and the vent valve is a flexible diaphragm sealed at one circumferential edge and having an annular portion proximate the other circumferential edge adapted to rest against the valve seat ridge when the vent valve is closed.

8. The valve defined in claim 7 wherein the vent valve includes means bearing against the diaphragm for forming the valve seat contacting portion of the diaphragm into a generally planar configuration.

9. The valve defined in claim 7 wherein the vent valve includes means resiliently biasing the diaphragm into closing contact with the vent valve seat ridge.

10. The valve defined in claim 9 wherein the main valving means includes means extending proximate the inlet to the main passage for being moved by fluid pressure applying means inserted into said inlet for thereby opening the main valve.

11. The valve defined in claim 10 wherein the main valving means is a generally cylindrical plug loosely received in the main passage having a shoulder extending outwardly therefrom and the main passage formed in the body has a larger diameter bore and a smaller diameter bore, the juncture therebetween forming a valve seat, the shoulder being disposed in the larger bore adjacent the seat for movement into contact with the seat for closing the main valve and away from the seat for opening the valve.

12. The valve defined in claim 11 wherein the means extending to proximate the inlet comprises as extension of the cylindrical plug toward the inlet from the shoulder thereon, whereby upon insertion of the fluid pressure applying means into the inlet the plug is moved away from the inlet thereby moving the shoulder away from the seat and opening the main passage valve.

13. The valve defined in claim 12 wherein the inlet is a luer tip inlet adapted to receive a leur tip tightly therein in fluid communication with the main passage and wherein the means extending proximate the inlet for opening the main valve includes means for being engaged by the luer tip for thereby opening the main valve upon insertion of a luer tip into the inlet.

14. The valve defined in claim 3 wherein the main valving means is a generally cylindrical plug loosely received in the main passage having a shoulder extending outwardly therefrom and the main passage formed in the body has a larger diameter bore and a smaller diameter bore, the juncture therebetween forming a valve seat, the shoulder being disposed in the larger bore adjacent the seat for movement into contact with the seat for closing the main valve and away from the seat for opening the valve.

15. The valve defined in claim 14 wherein the means extending to proximate the inlet comprises an extension of the cylindrical plug toward the inlet from the shoulder thereon, whereby upon insertion of the fluid pressure applying means into the inlet the plug is moved away from the inlet thereby moving the shoulder away from the seat and opening the main passage valve.

16. The valve defined in claim 15 wherein the main valve includes means resiliently biasing the shoulder toward the seat.

17. The valve defined in claim 15 wherein the inlet is a luer tip inlet adapted to receive a leur tip tightly therein in fluid communication with the main passage and wherein the means extending proximate the inlet for opening the main valve includes means for being engaged by the luer tip for thereby opening the main valve upon insertion of a luer tip into the inlet.

18. A relief valve comprising:
a valve body having fluid inlet and fluid outlet means connected by means forming a main passage;
main valve means between said inlet and outlet normally closing the main fluid passage, said main valve means including means extending proximate the inlet to the main passage for being moved by fluid pressure applying means inserted into said inlet for thereby opening the main valve;
vent passage means in fluid communication with the main passage on the inlet side of the main valve means and with the exterior of the valve body;
vent valve means normally closing the vent passage means, said vent valve means comprising flexible pressure responsive means in fluid communication with the main passage whereby said vent valve automatically opens the vent passage in response to pressure applied thereto when the pressure in the inlet side of the main passage applied through said vent passage to the flexible means reaches a predetermined value to thereby prevent fluid pressure of greater than said predetermined value from being applied at the outlet of the main fluid passage, said flexible means including an annular diaphragm surrounding the means forming the main passage;
a bypass passage in fluid communication with the main passage between the main valve and the inlet whereby the vent system is in fluid communication with the outlet only when the main valve is open;
a vent valve seat formed as an annular ridge in the body around the means forming the main passage; and
vent valve means including a flexible diaphragm sealed at one circumferential edge and having an annular portion proximate the other circumferential edge adapted to rest against the valve seat edge when the vent valve is closed.

19. The valve defined in claim 18 wherein the main valve means is a generally cylindrical plug loosely received in the main passage having a shoulder extending outwardly therefrom and the main passage formed in the body has a larger diameter bore and a smaller diameter bore, the juncture therebetween forming a valve seat, the shoulder being disposed in the larger bore adjacent the seat for movement into contact with the seat for closing the main valve and away from the seat for opening the valve.

20. The valve defined in claim 19 wherein the inlet is a luer tip inlet adapted to receive a luer tip tightly therein in fluid communication with the main passage.

21. The valve defined in claim 19 wherein the main valve means includes means extending proximate the inlet to the main passage for being moved by fluid pressure applying means inserted into said inlet for thereby opening the main valve.

22. The valve defined in claim 21 wherein the inlet is a luer tip inlet adapted to receive as the pressure applying means a luer tip tightly therein in fluid communication with the main passage, and wherein the means extending proximate the inlet for opening the main valve includes means for being engaged by the luer tip for thereby opening the main valve upon insertion of luer tip into the inlet.

23. The valve defined in claim 22 wherein the main valve means is a generally cylindrical plug loosely received in the main passage having a shoulder extending outwardly therefrom and the main passage formed in the body has a larger diameter bore and a smaller diameter bore, the juncture therebetween forming a valve seat, the shoulder being disposed in the larger bore adjacent the seat for movement into contact with the seat for closing the main valve and away from the seat for opening the valve.

24. The valve defined in claim 23 wherein the means extending to proximate the inlet comprises an extension of the cylindrical plug toward the inlet from the shoulder thereon, whereby upon insertion of the luer tip into the inlet the plug is moved away from the inlet thereby moving the shoulder away from the seat and opening the main passage valve.

* * * * *

UNITED STATES PATENT AND TRADEMARK OFFICE
CERTIFICATE OF CORRECTION

PATENT NO. : 4,044,793
DATED : August 30, 1977
INVENTOR(S) : Kenneth Keith Krueger & Todor Pavlov It is certified that error appears in the above-identified patent and that said Letters Patent are hereby corrected as shown below:

Col. 3, line 57, "whick" should be -- which --

Col. 4, line 24, "number" should be -- member --

Claim 14, line 44, "3" should be -- 13 --

Signed and Sealed this

Fourth Day of April 1978

[SEAL]

Attest:

RUTH C. MASON
Attesting Officer

LUTRELLE F. PARKER
Acting Commissioner of Patents and Trademarks